United States Patent
Sølvhøj et al.

(10) Patent No.: US 11,370,750 B2
(45) Date of Patent: Jun. 28, 2022

(54) DEMETHYLATION OF METHYL ESTER OF METHIONINE AND ITS HYDROXY ANALOG

(71) Applicant: Haldor Topsøe A/S, Kgs. Lyngby (DK)

(72) Inventors: Amanda Birgitte Sølvhøj, Værløse (DK); Esben Taarning, Frederiksberg (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 16/965,421

(22) PCT Filed: May 13, 2019

(86) PCT No.: PCT/EP2019/062194
§ 371 (c)(1),
(2) Date: Jul. 28, 2020

(87) PCT Pub. No.: WO2019/219597
PCT Pub. Date: Nov. 21, 2019

(65) Prior Publication Data
US 2021/0078945 A1    Mar. 18, 2021

(30) Foreign Application Priority Data
May 18, 2018  (DK) .......................... PA 2018 00223

(51) Int. Cl.
*C07C 319/20* (2006.01)
*C07C 319/18* (2006.01)

(52) U.S. Cl.
CPC .......... *C07C 319/20* (2013.01); *C07C 319/18* (2013.01)

(58) Field of Classification Search
CPC ........................... C07C 319/20; C07C 319/18
See application file for complete search history.

(56) References Cited

U.S. PATENT DOCUMENTS

| | | | |
|---|---|---|---|
| 3,247,278 A * | 4/1966 | Garwood | C07C 39/04 423/443 |
| 5,386,056 A | 1/1995 | Matsutoka | |
| 5,973,200 A | 10/1999 | Koenig | |
| 10,189,778 B2 | 1/2019 | Sadaba Zubiri et al. | |
| 2010/0121096 A1 | 5/2010 | Taarning et al. | |
| 2013/0072713 A1* | 3/2013 | Hagiya | C07C 319/20 562/559 |

FOREIGN PATENT DOCUMENTS

| | | | |
|---|---|---|---|
| CN | 1084511 A | 3/1994 | |
| CN | 1244192 A | 2/2000 | |
| CN | 107531619 A | 1/2018 | |
| KR | 2016129258 A * | 11/2016 | ............ C08F 220/06 |
| WO | 9832735 A1 | 7/1998 | |
| WO | 2016174231 A1 | 11/2016 | |

OTHER PUBLICATIONS

International Search Report and Written Opinion issued in corresponding International Patent Application No. PCT/EP2019/062194, 13 pages (dated Jul. 17, 2019).

Office Action (Text of the First Office Action) dated Nov. 23, 2021 by the China National Intellectual Property Administration of the People's Republic of China in corresponding Chinese Patent Application No. 201980015400.0, and an English Translation of the Office Action. (8 pages).

* cited by examiner

*Primary Examiner* — Rosalynd A Keys
(74) *Attorney, Agent, or Firm* — Buchanan Ingersoll & Rooney P.C.

(57) ABSTRACT

The following invention regards a process of demethylating a methyl ester of methionine or its hydroxy analog and producing methane thiol as a side-product. The methionine and its hydroxy analog are suitable as an animal feed additive and as a food additive. The methane thiol may be consumed in a hydrothiolation step such as in a step of preparing the methyl ester of methionine or its hydroxy analog from methyl vinyl glycolate.

24 Claims, No Drawings

DEMETHYLATION OF METHYL ESTER OF METHIONINE AND ITS HYDROXY ANALOG

FIELD OF THE INVENTION

The present invention regards a process for transforming the methyl ester of either methionine (Me-MET) or methionine hydroxy analog (Me-MHA) into the anion of the respective corresponding carboxylic acid (methionine, MET/methionine hydroxy analog, MHA) by reacting it with a hydrogen sulfide anion (HS⁻) while causing the production of methane thiol (MeSH). It further regards a process for transforming methyl vinyl glycolate (MVG), or the amino analog of MVG (MVG-AA) to Me-MHA or Me-MET respectively, by reacting it with MeSH and subsequently transforming the Me-MET or Me-MHA into the anion of the corresponding carboxylic acid (MET/MHA) by reacting it with a hydrogen sulfide anion (HS⁻) under the production of methane thiol (MeSH); and recovering the produced MeSH and using it as a reagent in the first step of the process.

BACKGROUND

In animal nutrition there is a great demand for feed additives. In particular, there is a demand for feed additives made from sustainable raw materials, such as carbohydrates. The amino acid Methionine (MET) and its alpha-hydroxy analog (MHA) are widely used as additives in animal feed. In order to be useful as feed additives, low cost processes for producing the amino acids or the alpha-hydroxy analogs thereof are needed. Known processes include fermentation and various processes of chemical synthesis.

In WO 2016/174231 a chemo-catalytic process is disclosed for the preparation of MHA and esters thereof. It comprises contacting one or more sugars with a metallo-silicate material in the presence of a compound comprising sulfur and a solvent. A preferred sulfur compound for use in the process is methane thiol and a preferred solvent is methanol. When methane thiol and methanol are used, the product obtained is the methyl ester of the methionine hydroxy analog (Me-MHA).

In WO 9832735 a process for the formation of Me-MHA through the hydrothiolation of MVG is disclosed. It consists of contacting methyl 2-hydroxybut-3-enoate (MVG) with methane thiol in the presence of a suitable radical initiator. The MVG substrate can be produced from sustainable raw materials as described in e.g. US 2010121096 where a chemo-catalytic process for the preparation of MVG is disclosed. It comprises contacting one or more sugars with a metallo-silicate material in the presence of a solvent. When methanol is used as solvent, the product obtained is the methyl 2-hydroxybut-3-enoate (MVG).

Methane thiol (also known as methyl mercaptan) is a useful chemical. However, it is classified as extremely flammable, very toxic and dangerous to the environment. Therefore handling of methane thiol requires a high degree of precautions.

The methyl ester of the methionine hydroxy analog is at present not used directly as feed additive for animals. It is desirable to remove the methyl ester group, in order for the end product to be suitable for industrial application within the field of animal nutrition. It is also desirable to reduce the need for handling toxic and hazardous chemicals. There is thus a need for low cost, environmentally friendly and industrially applicable processes for removing the ester group.

SUMMARY OF THE INVENTION

One obvious way of transforming a methyl ester into the corresponding carboxylic acid would be by direct hydrolysis under either acidic or alkaline aqueous conditions, usually by application of heat. Commonly used reagents for such transformation include sodium hydroxide for an alkaline hydrolysis or sulfuric acid for an acidic hydrolysis respectively, but a wide array of acids and bases may be employed. The reagents are cheap and the reactions are reliable in the cases where the methyl ester substrates are not sensitive towards acid/base, water and/or heat. Other methods of de-esterification are also known, such as the use of alkyl or benzyl thiolates, the use of iodotrimethylsilanes and the use of anhydrous trifluoracetic acid, among many others.

The inventors surprisingly found that demethylation of the methyl esters Me-MET and Me-MHA with a hydrogen sulfide anion resulted in high yields of the corresponding carboxylates along with equimolar amounts of methane thiol, making this procedure an excellent candidate for producing methionine products suitable as animal feed additives, while at the same time producing the chemical methane thiol as a useful co-product.

According to an aspect of the present invention a process is provided for producing a demethylation product of the formula (II):

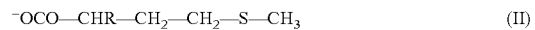

wherein R is —OH or —NH₂,
comprising a demethylation step of reacting a methyl ester of the formula (I):

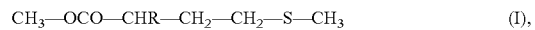

wherein R has the same meaning as above,
with a hydrogen sulfide anion to obtain methane thiol and the demethylation product of the formula (II).

The present process shows very good performance. The yields of the carboxylates are very high and in addition MeSH is formed. Forming MeSH as a co-product has several advantages. MeSH is volatile and accordingly it may easily be separated from the reaction mixture to obtain a high purity methionine product. In addition, MeSH is a valuable chemical and may be used or sold. According to an embodiment of the present invention the MeSH is recovered. According to another embodiment of the present invention the MeSH recovered and is used in a hydrothiolation step.

One use of MeSH is for transforming MVG, or the amino analog of MVG (MVG-AA), to the Methyl ester of Methionine Hydroxy Analog (Me-MHA) or the methyl ester of methionine (Me-MET) by reacting it with MeSH. MeSH is a preferred source of sulphur for this transformation. However, it is also a problematic raw material, since it is very volatile and hazardous. The Methyl ester of Methionine Hydroxy Analog (Me-MHA) and the methyl ester of methionine (Me-MET) may subsequently be deesterified.

According to an aspect of the present invention a process is provided for producing a demethylation product of the formula (II):

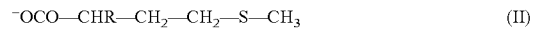

wherein R is —OH or —NH₂,
comprising:
a1) a hydrothiolation step of reacting a compound of the formula:

Wherein R has the same meaning as above, with methane thiol to obtain a methyl ester product of the formula (I):

$$CH_3-OCO-CHR-CH_2-CH_2-S-CH_3 \quad (I),$$

wherein R has the same meaning as above, and then
b) a demethylation step of reacting the methyl ester product of the formula (I) with a hydrogen sulfide anion to obtain methane thiol and the demethylation product of the formula (II).

In addition to the previous advantages, this process has the further advantage, that the MeSH obtained in the demethylation step may be used in the hydrothiolation step (a1). Since the stoichiometric relationship between each of the reactants MVG/MVG-AA and methane thiol as well as the product Me-MHA/Me-MET in step a1) of the process above is 1:1:1, and accordingly the stoichiometric relationship between the reactants hydrogen sulfide anion and Me-MHA/Me-MET as well as the products MHA/MET and methane thiol in step b) of the process above is also 1:1:1:1, the amount of MeSH used in the hydrothiolation step (a1) more or less equals the amount of MeSH produced in the demethylation step (b). However, in practice it may be needed to supplement with additional MeSH. In the hydrothiolation step a suitable catalyst or radical initiator may be used. If the hydrothiolation step and the demethylation step are conducted within battery limits, transporting of this hazardous chemical may be dispensed with. In this case the MeSH uncovered may be circulated directly to the hydrothiolation step.

MeSH may also be used in a metallo-silicate catalyzed process of converting sugars (including glycolaldehyde) into the Methyl ester of Methionine Hydroxy Analog (Me-MHA), which may be deesterified.

According to an aspect of the present invention a process is provided for producing a product of the formula (II):

$$^-OCO-CHR-CH_2-CH_2-S-CH_3 \quad (II)$$

wherein R is —OH
comprising:
  a2) a metallo-silicate catalyzed step of contacting a sugar with a metallo-silicate material in the presence of methanol and methane thiol to obtain a methyl ester product of the formula (I):

$$CH_3-OCO-CHR-CH_2-CH_2-S-CH_3 \quad (I),$$

wherein R has the same meaning as above, and then
b) a demethylation step of reacting the methyl ester of the formula (I) with a solvated hydrogen sulfide anion to obtain methane thiol and the demethylation product of the formula (II).

In addition to the previous advantages, this process has the further advantage, that the MeSH produced in the demethylation step may be used in the metallo-silicate catalyzed step.

Generally, the demethylation step is carried out in a demethylation reaction zone. Generally, the hydrothiolation step is carried out in a hydrothiolation reaction zone. Generally, the metallo-silicate catalyzed step is carried out in a metallo-silicate catalyzed reaction zone. Advantageously the MeSH produced in the demethylation reaction zone may be recirculated to the metallo-silicate catalyzed reaction zone or the hydrothiolation reaction zone. According to an embodiment of the present invention the methane thiol recovered from the demethylation reaction zone is recirculated to the hydrothiolation reaction zone (a1) or the metallo-silicate catalyzed reaction zone (a2). This is particularly advantageous when both steps are conducted as continuous processes.

The demethylation product may be recovered after the demethylation step in the form of the carboxylic acid or a carboxylate salt thereof.

The hydrothiolation step and the demethylation step may be combined into a single process step.

According to an aspect of the present invention, a process is provided of producing a demethylation product of the formula (II):

$$^-OCO-CHR-CH_2-CH_2-S-CH_3 \quad (II)$$

wherein R is —OH or —NH$_2$,
comprising:
  c) an integrated step of reacting a compound of the formula (III):

$$CH_3-OCO-CHR-CH=CH_2 \quad (III),$$

Wherein R has the same meaning as above,
  in the presence of methane thiol and a hydrogen sulfide anion to obtain the demethylation product of the formula (II).

In addition to the previous advantages, the integrated step has the further advantage of combining in one pot both a demethylation step and a hydrothiolation step, producing the demethylation product of the formula (II). Furthermore, in this aspect of the invention, the methane thiol produced in the demethylation step is consumed in the hydrothiolation step, thereby avoiding the need for recovering and transporting (such as recirculating) the methane thiol.

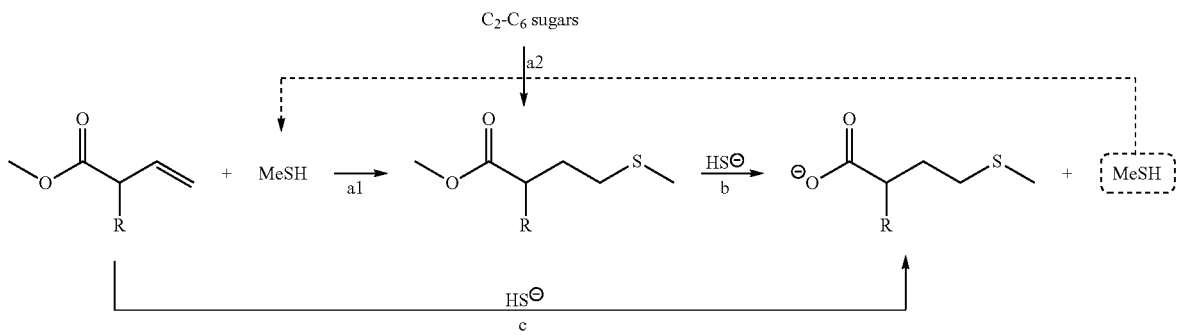

R = OH, NH$_2$

In the context of the present invention the individual steps on the figure above are referred to as:

Step a1 is referred to as the hydrothiolation step.
Step a2 is referred to as the metallo-silicate catalyzed step.
Step b is referred to as the demethylation step.
Step c is referred to as the integrated step

DETAILED DESCRIPTION OF THE INVENTION

Definitions

In the context of the present invention, the following terms are used:

| Abbr. | Also named as | Systematic name | Structure |
| --- | --- | --- | --- |
| Me-MET | Methionine Methyl Ester | 2-amino-4-methyl-sulfanyl-butyric acid methyl ester | 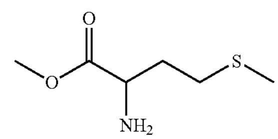 |
| Me-MHA | Methionine Hydroxy Analog Methyl Ester | 2-hydroxy-4-methylsulfanyl-butyric acid methyl ester | 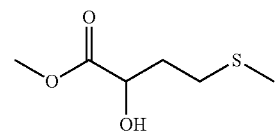 |
| MeSH | Methyl mercaptan | Methane thiol | 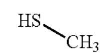 |
| MET | Methionine | 2-amino-4-methyl-sulfanyl-butyric acid | 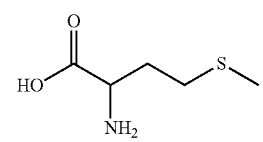 |
| MHA | Methionine Hydroxy Analog | 2-hydroxy-4-methylsulfanyl-butyric acid | 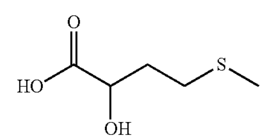 |
| MVG | Methyl Vinyl Glycolate | Methyl 2-hydroxy-but-3-enoate | 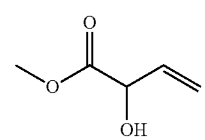 |
| MVG-AA | MVG Amino Analog | Methyl 2-amino-but-3-enoate | 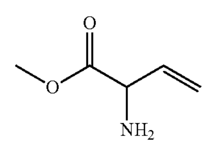 |
| Na-MET | Sodium salt of Methionine | Sodium 2-amino-4-methylsulfanyl-butyrate | 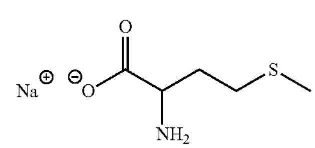 |
| Na-MHA | Sodium salt of Methionine Hydroxy Analog | Sodium 2-hydroxy-4-methylsulfanyl-butyrate | 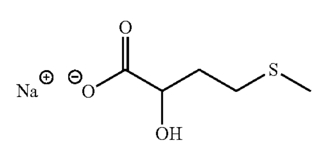 |
| X-MET | Metal salt of Methionine | (Metal) 2-amino-4-methylsulfanyl-butyrate | 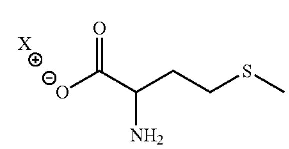 |

-continued

| Abbr. | Also named as | Systematic name | Structure |
|---|---|---|---|
| X-MHA | Metal salt of Methionine Hydroxy Analog | (Metal) 2-hydroxy-4-methyl-sulfanyl-butyrate | ![X-MHA structure: X⊕ ⊖O-C(=O)-CH(OH)-CH2-CH2-S-CH3] |

The term "methionine product" is meant to refer to either of MET, MHA and the salts thereof (X-MET or X-MHA).

The term "Recovering" is meant to refer either to collecting the product or to directing the product to a subsequent step or recirculating it to a previous step.

The term "yield" is in the present context meant to refer to moles of product formed per moles of reactant added to the reaction mixture (e.g. moles of compound (II) formed per moles of compound (I) present initially).

The terms "reactant" and "substrate" are used interchangeably to refer to the (unreacted) compounds fed to the reaction in question (e.g. demethylation or hydrothiolation).

The term "conversion" is in the present context meant to refer to the molar fraction of substrate which has reacted.

The term "continuous conditions" or "continuous process" is meant to refer to truly continuous process conditions with continuous feeding of substrate and continuous recovery of product (such as in a fluid bed reactor or packed bed reactor, optionally with recycle of excess second compound to the feed stream or to the reactor inlet) but it is also meant to refer to semi-continuous process conditions such as repeatedly feeding small portions to the reaction zone and repeatedly recovering small portions of the product from the reaction zone.

In the present context, a "reaction zone" is meant to refer to the area wherein the reaction takes place. In certain embodiments the reaction zone may be defined by the walls of a chemical reactor. In a continuous reactor, the reaction zone may be defined by the reactor walls and the inlet and the outlet. The reaction zone may be defined by the reaction mixture contained within the reactor.

The "reaction mixture" is meant to refer to the mixture present in the reaction zone, including both unreacted compounds and the products formed and any catalysts, by-products or solvents or diluents present.

Where nothing else is stated, the group R is —OH or —NH$_2$.

The term "hydrogen sulfide anion" is meant to refer to the anion HS$^-$ which is the sulfur analog of the hydroxide anion. It is implicit that a counter ion is also present whenever the hydrogen sulfide anion is present so that an overall charge neutrality is maintained.

The Demethylation Step

An advantage of the present invention is that under ambient reaction conditions the side product MeSH is volatile and may be recovered easily from the demethylation reaction mixture, since the other reaction products are in liquid or solid phase. This can be achieved by stripping the reaction mixture with a gas to drive out dissolved gaseous methane thiol and collecting methane thiol from the gas by condensing it out. Suitable gases for stripping include N$_2$, CH$_4$, H$_2$O (steam), CH$_3$OH (methanol vapor), CO$_2$ and H$_2$. Alternatively, methane thiol may be recovered by reducing the pressure to allow gaseous methane thiol to be released and collecting it by condensation or compressing it out to a liquid. Optionally, the collected methane thiol may be purified by e.g. distillation to remove hydrogen sulfide and other gaseous contaminants prior to further use.

The Hydrogen Sulfide Anion

According to an embodiment of the present invention the hydrogen sulfide anion is provided in the form of a hydrogen sulfide salt, such as a hydrogen sulfide metal salt. In an embodiment of the present invention the hydrogen sulfide salt is a metal salt, wherein the metal is an alkali metal or an earth alkali metal. The anion may be formed by dissolving a salt of the formula XSH (where X=Li, Na, K) or the formula X(SH)$_2$ (where X=Ca, Mg) in one of the reactants or in a solvent such as a demethylation solvent to obtain a solvated hydrogen sulfide anion. In an embodiment of the present invention the hydrogen sulfide metal salt is selected from the group consisting of LiSH, NaSH, KSH, Ca(SH)$_2$, Mg(SH)$_2$; or combinations thereof. In a preferred embodiment of the process the source of the hydrogen sulfide anion is NaSH or KSH due to the lower price, better availability and ease of handling of these hydrogen sulfide anion sources.

Alternatively, the hydrogen sulfide anion may be formed by reacting hydrogen sulfide H$_2$S in situ in the demethylation reaction zone in the presence of an appropriate base such as, but not limited to, NaOH or KOH.

In an embodiment of the present invention, the two above methods of providing the hydrogen sulfide anion may be combined, such that a hydrogen sulfide salt is added to the demethylation reaction mixture and hydrogen sulfide is bubbled through the demethylation reaction mixture.

For instance, in the case where sodium hydrogen sulfide (NaSH) is solvated, the solvated ions are HS$^-$ and Na$^+$. It is also possible to generate hydrogen sulfide anions by reacting hydrogen sulfide (H$_2$S) with a base such as NaOH. In this case the hydrogen sulfide anion is generated not by direct solvation of a salt but by acid-base reaction between dissolved H$_2$S and HO$^-$ to generate HS$^-$ and H$_2$O. Due to the amphoteric nature of the hydrogen sulfide anion in many solvents, the three species H$_2$S, HS$^-$ and S$^{2-}$ will be present at the same time in the reaction mixture in different relative amounts. This relative distribution can be modified by adding acids or bases to the demethylation reaction mixture. The term "hydrogen sulfide anion" is therefore also meant to refer to mixtures of H$_2$S, HS$^-$ and S$^{2-}$ in which HS$^-$ constitutes more than 1% of the three species in solution.

The Demethylation Product

The demethylation product will mainly be present in the demethylation reaction mixture on ionic form. In an embodiment of the present invention the demethylation product obtained is recovered in the form of a carboxylic acid (MET or MHA) or a carboxylate salt (X-MET or X-MHA). It may be recovered from the demethylation reaction mixture by crystallization and separation of the salt from the depleted reaction mixture. Other options of recovering the demethylation product include chromatography, electrodialysis, acidification, distillation and extraction.

The Demethylation Reaction Mixture

According to an embodiment of the present invention, the demethylation reaction is carried out in a demethylation solvent. In such embodiment, the reaction mixture comprises unreacted hydrogen sulfide anion, unreacted methyl ester compound of formula (I), any demethylation product and methane thiol formed and a solvent. The preferred solvent is a polar solvent. A polar solvent is meant to refer to a composition having a dielectric constant exceeding 15, such as, but not limited to, DMSO, dimethylformamide, HMPA, acetonitrile, acetone, ethanol, methanol, water or mixtures thereof. An advantage of using polar or slightly polar solvents is that the solubility of the reagents, in particular the ionic compounds, are higher in polar solvents. The demethylation reaction mixture should in the demethylation reaction zone provide an environment which has a polarity favouring the solvated (or dissociated) form of the hydrogen sulfide salt.

In an embodiment of the present invention the demethylation step is carried out in the presence of a polar solvent having a dielectric constant in the range of from 15 to 100.

In an embodiment of the present invention the solvent is selected from the group consisting of DMSO, dimethylformamide, HMPA, acetonitrile, acetone, ethanol, methanol, water; or mixtures thereof.

According to another embodiment of the present invention, the process is performed without any solvent present. In that particular case the demethylation reaction mixture comprises the source of hydrogen sulfide anions and the methyl ester of the formula (I). An advantage of omitting the solvent is that it reduces the need of removing the solvent after the reaction. Furthermore, it enables the process to run at much higher concentrations.

In an embodiment of the present invention the demethylation step is carried out at a temperature in the range of from 0° C. to 200° C., such as at a temperature in the range of from 30° C. to 100° C. or 40-70° C.

In an embodiment of the present invention the demethylation step is carried out in a substantially oxygen free atmosphere, preferably at an oxygen partial pressure in the range of from 0.00001 bar (1 Pa) to 0.1 bar (10 kPa). An advantage of an oxygen free process is that the oxidation of the formed methane thiol is reduced or avoided.

According to an embodiment of the present invention, the demethylation step is carried out at a pressure in the range of from 0.1 bar (10 kPa) to 10 bar (1000 kPa).

According to an embodiment of the present invention, the initial molar ratio of hydrogen sulfide anion relative to the methyl ester of the formula (I) is in the range of from 1:100 to 100:1 in the initial reaction mixture. This is to be understood as the molar ratio between the hydrogen sulfide anion and the methyl ester of the formula (I) before they start reacting. When the process is carried out as continuous flow, the initial concentration is meant to refer to the concentration in the combined feed streams.

According to an embodiment of the present invention, all or some of the methane thiol recovered from the demethylation reaction zone is recirculated to the to the hydrothiolation reaction zone or the metallo-silicate catalyzed reaction zone. It may be separated as described previously by stripping, condensation and/or compression.

The Hydrothiolation Step

The free radical hydrothiolation of MVG with methane thiol is described in WO 9832735 A1. It consists of contacting methyl 2-hydroxy-but-3-enoate (MVG) with methanethiol in the presence of a suitable radical initiator. The MVG substrate can be produced from sugars according to US 2010121096 AA. The described procedure comprises contacting one or more sugars, such as sucrose, fructose, glucose or glycolaldehyde, with a metallo-silicate in the presence of a solvent.

The two steps can be combined in a single metallo-silicate catalyzed step as described in detail in WO 2016/174231. In brief, a sugar, such as sucrose, xylose, mannose, tagatose, galactose, glucose, fructose, sugar syrup, threose, erythrose, erythrulose, dihydroxyacetone, glyceraldehyde or glycolaldehyde is contacted with a metallo-silicate material in the presence of a solvent.

In an embodiment the metal in the metallo-silicate is selected from group consisting of tin, titanium, zirconium and hafnium, or mixtures thereof. In an embodiment the silicate material has a beta-zeolite structure. In an embodiment the solvent is methanol, possibly with 0.1-10% water. The reaction is performed in the presence of MeSH to form Me-MHA.

The formation of MVG from sugar and the subsequent hydrothiolation of MVG to Me-MHA may take place in a single reaction zone, or the two steps may be conducted in separate reaction zones. The solvent may be removed prior to the hydrothiolation step.

The Continuous Process

The process according to the present invention may be conducted as a continuous flow process or a batch process. In the present context, a continuous flow process is to be understood as a reaction or process that occurs over a prolonged period of time, and the reactant is continuously fed through a reaction chamber in a solvent. It is an advantage of a continuous flow process that it is suitable for large scale production.

According to an embodiment of the present invention, the demethylation step is conducted as a batch or a fed-batch process. In an embodiment, Me-MET or Me-MHA are contacted with a source of hydrogen sulfide anions in a reaction zone under conditions suitable to carry out the demethylation reaction. The reactants are held in the reaction zone until sufficient demethylation has been achieved. The demethylation step can be carried out under varying different reaction parameters such as the ratio of hydrogen sulfide anion to Me-MET or Me-MHA, reaction temperature, solvent/no solvent, reaction time, pH, pressure, atmosphere, etc.

According to an embodiment of the present invention, the demethylation step is conducted as a continuous process and the methyl ester of the formula (I) and the hydrogen sulfide anion are continuously provided to a demethylation reaction zone; and the methane thiol and the demethylation product formed in the demethylation reaction zone are continuously recovered from the demethylation reaction zone.

Me-MET or Me-MHA may be contacted with a source of hydrogen sulfide anions in a demethylation reaction zone; this can be done by continuously feeding a feed stream containing Me-MET or Me-MHA and a feed stream containing a source of sulfide anions or hydrogen sulfide to the demethylation reaction zone and reacting the reaction mixture in the reaction zone at the desired reaction conditions and continuously recovering a demethylation product stream from the demethylation reaction zone. The demethylation step can be carried out under varying different reaction parameters such as the ratio of hydrogen sulfide anion to Me-MET or Me-MHA, reaction temperature, solvent/no solvent, reaction time, pH, pressure, etc. The demethylation product stream is exiting the reaction zone at a flow (kg/hr) similar to that which enters the reaction zone (total of product streams equals total of feed streams).

According to an embodiment of the present invention, methane thiol may be recovered from the demethylation product stream. This can be achieved by stripping the demethylation product stream with a gas to drive out dissolved gaseous methane thiol and collecting some or all of the methane thiol from the gas by condensing it out. Suitable gases for stripping include $N_2$, $CH_4$, $H_2O$ (steam), $CH_3OH$ (methanol vapor), $CO_2$ or $H_2$. Alternatively, methane thiol may be recovered by reducing the pressure to allow gaseous methane thiol to be released and collecting it by condensation or compressing it out to a liquid. Optionally, the collected methane thiol may be purified by e.g. distillation to remove hydrogen sulfide and other gaseous contaminants prior to further use.

According to an embodiment of the present invention, the demethylation reaction product (Na-MET or Na-MHA in the case where NaSH was used as hydrogen sulfide anion source) may be recovered from the methane thiol depleted demethylation product stream by crystallization and separation of the salt from the methane thiol depleted demethylation product stream. Other options of recovering the demethylated product include chromatography, electrodialysis, acidification, distillation and extraction.

According to an embodiment of the present invention, the hydrothiolation step is conducted as a continuous process and the compound of formula (Ill) and methane thiol are provided to a hydrothiolation reaction zone in one or more feed streams; and the methyl ester product of formula (I) formed in the hydrothiolation reaction zone is recovered from the reaction zone in a hydrothiolation product stream which is led to the demethylation reaction zone for conversion into a demethylation product of formula (II) which product is recovered in a demethylation product stream.

Animal Feed Additive

The methionine product of the present invention is useful as animal feed additive and as food additive as such. Optionally, the demethylation product may be acidified, using e.g. sulfuric acid, to transform it into the acid form (X-MET or X-MHA to MET or MHA, respectively) or it may be ion exchanged to transform it into a more desirable salt for feed application, such as $Ca(MET)_2$ or $Ca(MHA)_2$.

For both uses they may be mixed with one or more animal feed or human food components, such as a carrier material, a carbohydrate, an adjuvant, an anti-caking agent, an antioxidant, and/or a surfactant, to form an animal feed or food composition. The additives or compositions may be formulated into a solution, suspension, pellets, powder etc. as is known in the art.

EXAMPLE

In a Schlenk flask was placed Sodium Hydrogen Sulfide monohydrate and a magnetic stirbar. The flask was evacuated and purged with nitrogen 3 times to remove any oxygen.

A solution of Me-MHA (methyl ester product of formula (I) with R=—OH) in the solvent DMSO was added to the flask via a syringe. The flask was lowered into an oil bath and the reaction mixture was stirred at the desired temperature under a nitrogen atmosphere for 24 hours.

GC analysis of the solution before and after reaction showed up to 100% conversion of methyl 2-hydroxy-4-methylthio-butanoate after 24 hours. GCMS confirmed the formation of methane thiol. NMR analysis confirmed the presence of 2-hydroxy-4-methylthio-butanoic acid in up to 93% yield.

It appears that the selectivity towards the sodium carboxylate product increases significantly when the temperature is increased from room temperature to 50° C.

| Substrate (I), R = —OH | | Solvent | | HS⁻ source | | T | Conv. | Yield* | MeSH observ |
|---|---|---|---|---|---|---|---|---|---|
| MMHA | 1.00 mmol | DMSO | 825 µl | NaSH | 1.34 mmol | r.t. | 90% | 15% | Y |
| MMHA | 0.96 mmol | DMSO | 825 µl | NaSH | 1.69 mmol | 50° C. | 100% | 93% | Y |
| MMHA | 0.96 mmol | DMSO | 825 µl | — | — | r.t. | 20% | 0% | N |
| — | — | DMSO | 1000 µl | NaSH | 2.05 mmol | 50° C. | — | — | N |

*Yield refers to the molar yield of the carboxylate relative to the added methyl ester substrate

The invention claimed is:

1. A process of producing a demethylation product of the formula (II):

$$^-OCO\text{—}CHR\text{—}CH_2\text{—}CH_2\text{—}S\text{—}CH_3 \qquad (II)$$

wherein R is OH or —$NH_2$,
comprising a demethylation step of reacting a methyl ester of the formula (I):

$$CH_3\text{—}OCO\text{—}CHR\text{—}CH_2\text{—}CH_2\text{—}S\text{—}CH_3 \qquad (I),$$

wherein R has the same meaning as above,
with a hydrogen sulfide anion to obtain methane thiol and the demethylation product of the formula (II),
comprising recovering the methane thiol formed in the demethylation step,
wherein the methane thiol recovered is used in a hydrothiolation step.

2. A process of producing a demethylation product of the formula (II):

$$^-OCO\text{—}CHR\text{—}CH_2\text{—}CH_2\text{—}S\text{—}CH_3 \qquad (II)$$

wherein R is —OH or —$NH_2$,
comprising:
a1) a hydrothiolation step of reacting a compound of the formula (III):

$$CH_3\text{—}OCO\text{—}CHR\text{—}CH\text{=}CH_2 \qquad (III),$$

wherein R has the same meaning as above,
with methane thiol to obtain a methyl ester of the formula (I):

$$CH_3\text{—}OCO\text{—}CHR\text{—}CH_2\text{—}CH_2\text{—}S\text{—}CH_3 \qquad (I),$$

wherein R has the same meaning as above, and
b) a demethylation step of reacting the methyl ester of the formula (I) with a hydrogen sulfide anion to obtain methane thiol and the demethylation product of the formula (II),
comprising recovering the methane thiol formed in the demethylation step,
wherein the methane thiol recovered is used in a hydrothiolation step.

3. A process of producing a demethylation product of the formula (II):

$$^-OCO-CHR-CH_2-CH_2-S-CH_3 \quad (II)$$

wherein R is —OH
comprising:
a2) a metallo-silicate catalyzed step of contacting a sugar with a metallo-silicate material in the presence of methanol and methane thiol to obtain a methyl ester product of the formula (I):

$$CH_3-OCO-CHR-CH_2-CH_2-S-CH_3 \quad (I),$$

wherein R has the same meaning as above, and then
b) a demethylation step of reacting the methyl ester of the formula (I) with a hydrogen sulfide anion to obtain methane thiol and the demethylation product of the formula (II),
comprising recovering the methane thiol formed in the demethylation step,
wherein the methane thiol recovered is used in a hydrothiolation step.

4. The process according to claim 1, wherein the demethylation step is carried out in a demethylation reaction zone.

5. The process according to claim 1, wherein the hydrothiolation step is carried out in a hydrothiolation reaction zone.

6. The process according to claim 3, wherein the metallo-silicate catalyzed step is carried out in a metallo-silicate catalyzed zone.

7. The process according to claim 1, wherein the hydrogen sulfide anion is provided in the form of a hydrogen sulfide salt.

8. The process according to claim 7, wherein the hydrogen sulfide anion is a hydrogen sulfide metal salt selected from the group consisting of LiSH, NaSH, KSH, Ca(SH)$_2$, Mg(SH)$_2$; or combinations thereof.

9. The process according to claim 1, comprising recovering the demethylation product formed in the form of a carboxylic acid or a carboxylate salt.

10. The process according to claim 1, wherein the demethylation step is carried out in the presence of a demethylation solvent having a dielectric constant in the range of from 15 to 100.

11. The process according to claim 10, wherein the demethylation solvent is selected from the group consisting of DMSO, dimethylformamide, HMPA, acetonitrile, acetone, ethanol, methanol or water; or mixtures thereof.

12. The process according to claim 1, wherein the demethylation step is carried out at a temperature in the range of from 0° C. to 200° C.

13. The process according to claim 1, wherein the demethylation step is carried out at an oxygen partial pressure from 0.00001 to 0.1 bar (10 kPa).

14. The process according to claim 1, wherein the demethylation step is carried out at a pressure in the range of from 0.1 bar (10 kPa) to 10 bar (1000 kPa).

15. The process according to claim 1, wherein the initial molar ratio of hydrogen sulfide anion relative to the methyl ester of the formula (I) is in the range of from 1:100 to 100:1.

16. The process according to claim 6, comprising using all or some of the methane thiol recovered from the demethylation reaction zone in the hydrothiolation reaction zone and/or the metallo-silicate catalyzed zone.

17. The process according to claim 1, comprising recovering all or some unreacted hydrogen sulfide anion from the demethylation reaction zone.

18. The process according to claim 1, comprising recovering all or some unreacted methyl ester of the formula (I) from the demethylation reaction zone.

19. The process according to claim 1, wherein the demethylation step is conducted as a batch or a fed-batch process.

20. The process according to claim 1, wherein the demethylation step is conducted as a continuous process and the methyl ester of the formula (I) and the hydrogen sulfide anion are provided to a demethylation reaction zone; and the methane thiol and the demethylation product formed in the demethylation reaction zone are recovered from the demethylation reaction zone.

21. The process according to claim 1, wherein the hydrothiolation step is conducted as a continuous process and the compound of formula (III) and methane thiol are provided to a hydrothiolation reaction zone; and the methyl ester of the formula (I) formed in the hydrothiolation reaction zone is recovered from the hydrothiolation reaction zone in a stream which is led to the demethylation reaction zone.

22. The process according to claim 9, wherein the carboxylate salt is exposed to an ion exchange step.

23. The process according to claim 3, wherein solvent is used in the hydrothiolation step or the metallo-silicate catalyzed step and a step of removing some or all of the solvent is conducted between the hydrothiolation step or the metallo-silicate catalyzed step and the demethylation step.

24. A process of producing a demethylation product of the formula (II):

$$^-OCO-CHR-CH_2-CH_2-S-CH_3 \quad (II)$$

wherein R is —OH or —NH$_2$,
comprising:
c) an integrated step of reacting a compound of the formula (III):

$$CH_3-OCO-CHR-CH=CH_2 \quad (III),$$

wherein R has the same meaning as above,
in the presence of methane thiol and a hydrogen sulfide anion to obtain the demethylation product of the formula (II).

* * * * *